US00PP10729P

United States Patent [19]

Olesen et al.

[11] Patent Number: Plant 10,729

[45] Date of Patent: Dec. 22, 1998

[54] FLORIBUNDA ROSE PLANT NAMED 'POULGRET'

[75] Inventors: L. Pernille Olesen; Mogens N. Olesen, both of Fredensborg, Denmark

[73] Assignee: Poulsen Roser ApS, Fredensborg, Denmark

[21] Appl. No.: 864,849

[22] Filed: May 29, 1997

[51] Int. Cl.[6] ..... A01H 5/00

[52] U.S. Cl. ..... Plt./23

[58] Field of Search ..... Plt./23, 22

[56] References Cited

PUBLICATIONS

UPOV–ROM, 1997 Apr., Plant Variety Database, GTI Jouve Retrieval Software, Citations for 'POULgret'.

*Primary Examiner*—Howard J. Locker

[57] ABSTRACT

A new and distinct floribunda rose plant is disclosed which has abundant creamy white flowers, dark green glossy foliage, compact even growth, and rapid repeat flowering. The variety successfully propagates from softwood cuttings and is suitable for year round production in commercial glasshouses and nurseries. This new and distinct variety has shown to be uniform and stable in the resulting generations from such asexual propagation.

2 Drawing Sheets

SUMMARY OF THE INVENTION

The present discovery constitutes a new and distinct variety of floribunda rose plant which was discovered in a cultivated area. The mutation resulted from POULskov, a patented variety described and illustrated in U.S. Plant Pat. No. 9,062 and issued on Feb. 28, 1995. The variety resulted from a naturally occurring mutation of unknown causation discovered as a branch of a plant of 'POULskov' which was growing in a controlled planting. The variety was discovered in the autumn of 1990. The new variety is named 'POULgret'.

The rose plant of the present discovery has a unique combination of characteristics which are outstanding in the new variety and which distinguish it from the original rose 'POULskov' as well as all other varieties which we are aware of. For example, the new variety has:

1. Abundant uniform creamy white flowers with good durability and repeat bloom;

2. Attractive long lasting foliage and compact growth,

3. Year-round flowering under glasshouse conditions;

4. Suitability for production from softwood cuttings in pots;

5. Durable flowers and foliage which make the variety suitable for distribution in the floral and nursery industry.

This combination of qualities was lacking in floribunda rose varieties that were in commercial cultivation and the qualities have been substantially achieved in the new variety.

The resulting mutation was evaluated during the spring of 1991 in a controlled environment.

'POULgret' was selected by L. Pernille and Mogens N. Olesen in their rose development program in Fredensborg, Denmark in the summer of 1991.

Asexual reproduction of 'POULgret' by cuttings and traditional budding was first done by L. Pernille and Mogens N. Olesen in August, 1991. This initial and subsequent propagations have demonstrated that the characteristics of 'POULgret' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers, leaves, stems, and a plant of 'POULgret'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

Specifically illustrated in SHEET 2 is a closeup view of the blooms and foliage of the plant.

DETAILED DESCRIPTION OF THE VARIETY

The following is a detailed description of 'POULgret', as observed in its growth in glasshouses in Fredensborg, Denmark and Half Moon Bay, Calif. and in field nursery in Applegate, Oreg. Descriptions were made from plants treated with growth regulators normally used in the greenhouse production process. The growth regulator Paclobutrazol was applied at 30 ppm weekly for three weeks beginning at a plant age of 9 weeks. The peduncle lengths mentioned may actually be shorter and the foliage color several shades darker than on untreated specimens. Color references are made using The Royal Horticultural Society (London, England) Colour Chart, 1995.

For a comparison, the nearest existing rose variety is POULskov, a patented variety described and illustrated in U.S. Plant Pat. No. 9,062 and issued on Feb. 28, 1995. Chart 1 details several physical characteristics of 'POULgret' and the comparison variety.

Chart 1

| | 'POULgret' | 'POULskov' |
|---|---|---|
| Color of the flower bud at 1/4 | RHS 155 B of the White Color | Between RHS 49 C of the Red Color |

-continued

Chart 1

| | 'POULgret' | 'POULskov' |
|---|---|---|
| opening | Group | Group and RHS 55 D of the Red Color Group |
| Color of the upper surface of petal on an open flower | RHS 155 B of the White Color Group | Between RHS 49 D of the Red Color Group and RHS 56 B of the Red Color Group |
| Color of edge of upper side of petal on an open flower | RHS 155 B of the White Color Group | RHS 36 B of the Red Color Group |

Mutation resulting from: 'POULskov' (U.S. Plant Pat. No. 9,062).

Classification:

*Botanical.*—Rosa hybrida.

*Commercial.*—Floribunda.

Flower and Flower Bud

Blooming cycle: Recurrent.

Flower bud:

*Size.*—18–22 mm in length when petals are just beginning to crack open.

*Bud form.*—Pointed to ovoid.

*Bud color.*—R.H.S. 155 B of the White Color Group at ¼ opening.

*Sepals.*—Between R.H.S. 138 A and R.H.S. 138 B of the Green Group. Foliaceous appendages not present. Surfaces of sepals lightly pubescent. Stipitate glands present.

*Peduncle.*—Surface: Without prickles. Stipitate glands present. Length: 25–35 mm average length. Color: R.H.S. 139 C of the Green Color Group. Prickles: Lacking.

*Receptacle.*—Surface: Smooth. Glabrous. Shape: Funnel to urn shaped. Size: Small. 8 mm×7 mm. Color: R.H.S. 139 C of the Green Color Group.

*Borne.*—Sometimes singly, usually multiple to 3–5 buds per stem.

Flowering Stem:

*Length.*—25–35 cm.

Flower bloom:

*Diameter.*—Small to medium for its class. 50–60 mm on average.

*Form.*—Upon opening, ovate to rounded. Completely open a flattened convex with petals somewhat reflexed.

*Petalage.*—Semi-Double. Average range: 25–28 petals.

*Color.*—Upon opening, the upper surface is R.H.S. 155 B of the White Color Group. Upon opening, the reverse side is R.H.S. 155 B of the White Color Group. After opening, the upper surface is R.H.S. 155 B of the White Color Group. After opening, the reverse surface is R.H.S. 155 B of the White Color Group. A small petal spot R.H.S. 4 C of the Yellow Color Group exists on the inner side of the petal base. A very small petal spot R.H.S. 4 C of the Yellow Color Group exists on the outer side of the petal base.

*Margin.*—Petals reflex backwards slightly. Margin undulated.

*Variations.*—Uniform.

*Petaloids.*—2–5 small and delicate petaloids per flower. Color Group 155B.

*Fragrance.*—Limited apple-like fragrance.

*Duration.*—On the plant 12–15 days, as a cut flower 9–12 days.

Reproductive Organs:

*Pollen.*—Average abundance. Yellow-Orange Group 14B.

*Anthers.*—Size: Medium. Color: Yellow-Orange Group 14B.

*Filaments.*—Color: Greenish yellow R.H.S. 2 C of the Yellow Color Group.

*Stigmas.*—R.H.S. 2 D of the Yellow Color Group. Generally at same position as anthers.

*Styles.*—Color: White Group 155C.

Plant

Plant growth: Vigorous, compact, even, and bushy. When grown as a 15–17 cm pot plant, the average height of the plant itself is 22–25 cm and the average width is 26–28 cm. When grown as a nursery plant on its own roots, the average plant height is 70–80 cm and the average plant width is 75–90 cm.

Stems:

*Color.*—Young wood: R.H.S. 143 C of the Green Color Group. Older wood: R.H.S. 143 B of the Green Color Group.

*Prickles.*—Incidence: Moderate. Size: Average length: 7–8 mm. Color: Yellow-Green Group 145C with intonation of Greyed-Red Group 179C. Shape: Linear to concave.

*Bark.*—Young wood: Smooth. Older wood: Smooth.

Plant foliage:

*Normal number of leaflets on average leaves.*—Normally 5 leaflets, but 7 leaflets present on a number of leaves.

*Leaf size.*—Small to medium. 50×70 mm.

*Abundance.*—Above average abundance.

*Color, mature foliage.*—Upper leaf surface: Dark green. Between R.H.S. 137 A and 139 A of the Green Color Group. Lower leaf surface: Medium green. Between R.H.S. 138 A and 138 B of the of the Green Color Group.

*Color juvenile foliage.*—The upper leaf surface is Green Group 137A. The lower leaf surface is Yellow-Green Group 147B. Leaflet margin, leaf petiole, leaf rachis, and stipule of juvenile foliage have red intonation of Greyed-Red Group 179A.

Plant leaves and leaflets:

*Stipules.*—Present. 5–7 mm in length. Hairs present. Juvenile stipules are red or nearly so. Greyed-Red Group 179A. Mature stipules are Green Group 137B.

*Petiole.*—Length: 18–22 mm on leaves with 5 leaflets. Underneath: With prickles and stipitate glands. Color of prickles is Green-White Group 157B.

*Edge.*—Serrated.

*Shapes.*—Leaflets are ovate to rounded.

*Leaflets.*—Number: 5

*Other.*—Semi-glossy to glossy finish. Thick texture.

Disease resistance: Above average resistance to mildew, rust, and black spot under normal growing conditions in Half Moon Bay, Calif. and Fredensborg, Denmark and Applegate, Oreg.

We claim:

1. A new and distinct variety of rose plant of the floribunda class, substantially as herein illustrated and described, as a distinct and novel rose variety due to its abundant creamy white flowers, dark green glossy foliage, compact even growth, and rapid repeat flowering suitable for production from softwood cuttings in pots, durable flowers and foliage which make the variety suitable for distribution in the floral industry.

* * * * *

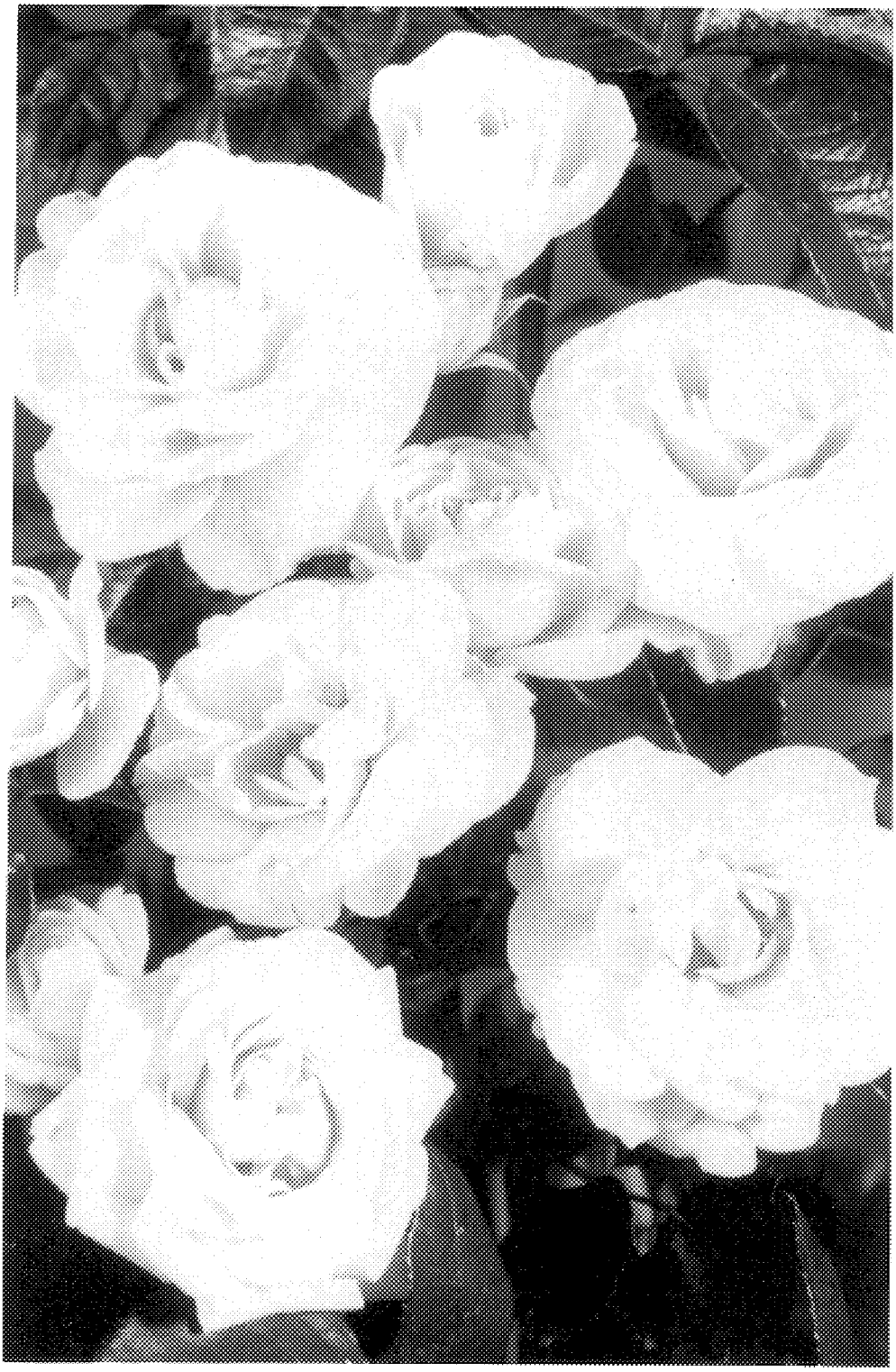

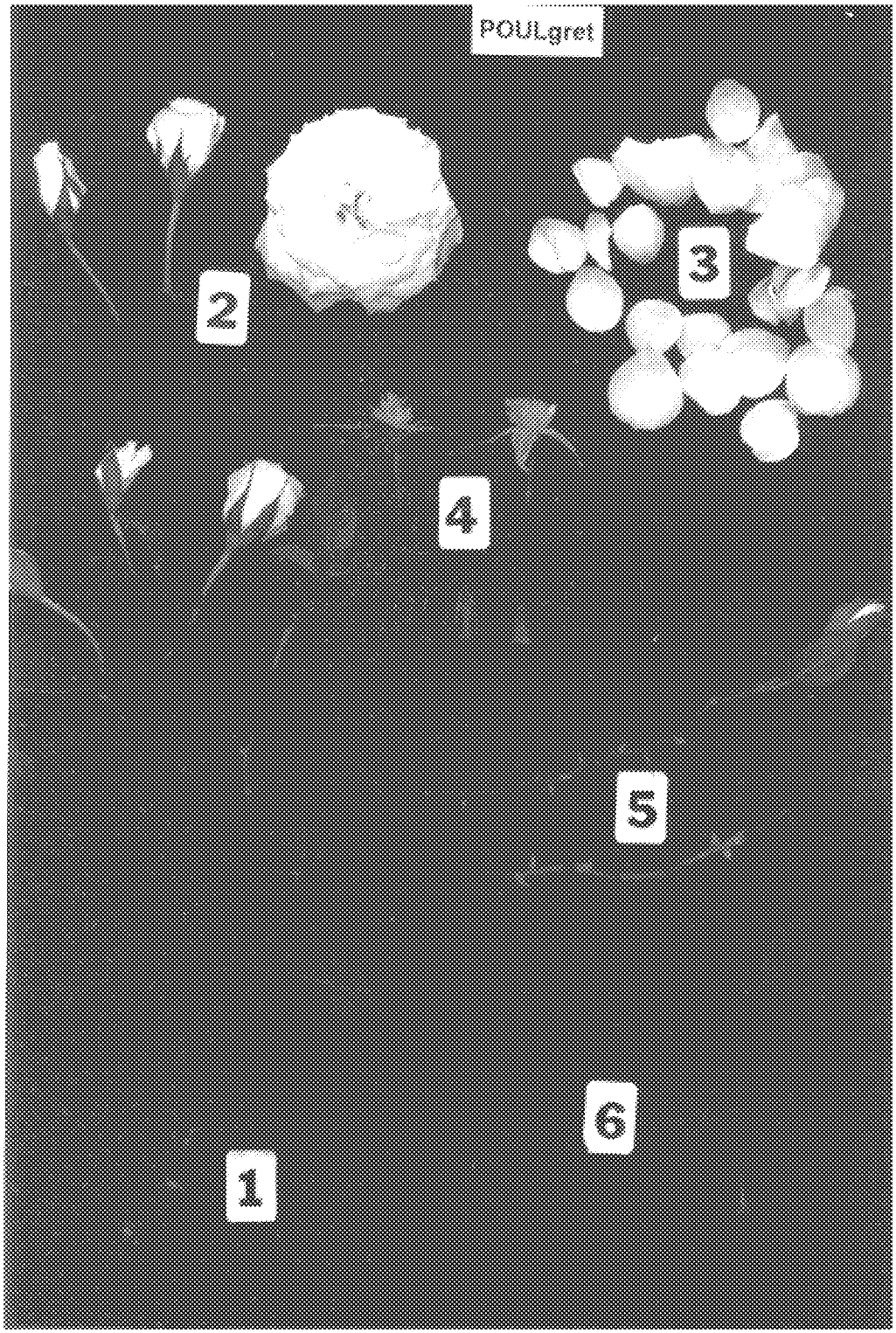
POULgret
2
3
4
5
6
1